United States Patent [19]

Rankin

[11] 4,199,567

[45] Apr. 22, 1980

[54] METHOD FOR IMPARTING FREEZE STABILITY TO CHLORHEXIDINE-CONTAINING MEDICAMENTS

[75] Inventor: Billy F. Rankin, Rockville, Md.

[73] Assignee: Burton, Parsons & Company, Inc., Washington, D.C.

[21] Appl. No.: 566

[22] Filed: Jan. 2, 1979

[51] Int. Cl.² ............... A61K 31/00; A61K 31/08; A61K 31/155; A61K 47/00
[52] U.S. Cl. ............................ 424/173; 424/326; 424/342
[58] Field of Search ............... 424/173, 326, 342

[56] References Cited

U.S. PATENT DOCUMENTS

| 3,152,181 | 10/1964 | Shapiro et al. | 424/326 |
| 3,767,788 | 10/1973 | Rankin | 424/78 |
| 3,843,782 | 10/1974 | Krezanoski et al. | 424/326 |
| 3,882,036 | 5/1975 | Krezanoski et al. | 424/78 |

OTHER PUBLICATIONS

J. Pharm. Pharmacol. 16, Suppl. 51T–55T (1964)—Brown et al.

*Primary Examiner*—Douglas W. Robinson
*Attorney, Agent, or Firm*—Fidelman, Wolffe & Waldron

[57] ABSTRACT

Chlorhexidine gluconate containing solutions are stabilized against precipitation upon freezing by the addition thereto of certain nonionic surfactants.

4 Claims, 3 Drawing Figures

METHOD FOR IMPARTING FREEZE STABILITY TO CHLORHEXIDINE-CONTAINING MEDICAMENTS

BACKGROUND OF THE INVENTION

This invention relates to a technique for imparting freeze stability to chlorhexidine - containing medicaments. More specifically, this invention provides a method for preventing chlorhexidine gluconate from precipitating as the hydrochloride from chloride ion-containing aqueous solutions upon exposure to freezing conditions.

Chlorhexidine, which is 1, 1'-Hexamethylene-bis [5-pchlorophenyl biguanidine], is a widely used topical antiseptic. Because of solubility considerations, chlorhexidine is often used in the form of its gluconate salt especially in aqueous base formulations.

An example of a widely used, chlorhexidine containing formulation is that of ophthalmic solutions. Ophthalmic solutions in general may serve as a wetting agent in the eye, that is, an artificial tear material useful for the treatment of "dry-eye" or as a cleaning, lubricating and cushioning agent for the eye after an injury or therapeutic surgery. Ophthalmic solutions are also routinely used as a cleaning, lubricating and cushioning agent for both hard and gel-type contact lenses.

Typically, ophthalmic solutions are isotonic, buffered to the required pH, sterile and contain additives and mediciments to control viscosity, enhance wettability and provide bactericidal activity. Isotonicity usually is provided by sodium chloride or mixtures of sodium and potassium chloride. Hence, ophthalmic solutions will typically contain a relatively high chloride ion concentration. Patents which are considered to disclose representative ophthalmic solutions include U.S. Pat. Nos. 3,882,036 and 3,549,747 to Krezanoski et al and U.S. Pat. No. 3,767,788 to Rankin.

While chlorhexidine gluconate has sufficient solubility to effectively act as a topical antiseptic agent in aqueous preparations such as ophthalmic solutions, its rather low solubility is further affected by pH, ionic strength and temperature. In particular, it has been found that if a chloride-ion containing solution of chlorhexidine gluconate is subjected to freezing, the chlorhexidine tends to precipitate out in the form of chlorhexidine hydrochloride. This latter compound is far less soluble than is chlorhexidine gluconate and does not again dissolve. Hence, preparations containing chlorhexidine gluconate and chloride ion are effectively ruined by freezing. The solution becomes cloudy due to the dispersion of finely divided particles of chlorhexidine hydrochloride thus rendering it unacceptable for consumer use or sale.

Products such as ophthalmic solutions are often exposed to freezing temperatures during transport and warehouse storage. Additionally, since these preparations are often carried in luggage during travel, exposure to freezing temperatures can occur under these circumstances.

SUMMARY OF THE INVENTION

Aqueous mediciment solutions containing chlorhexidine and chloride ion are rendered freeze-stable by inclusion within the formulation of a nonionic surfactant comprising a polyoxyethylene fatty acid ester having an HLB (hydrophile-lipophile balance) number greater than 11.

Hence, it is an object of this invention to prevent the precipitation of chlorhexidine gluconate from aqueous solutions upon exposure to freezing.

It is another object of this invention to render freeze-stable aqueous mediciment solutions containing both chlorhexidine gluconate and chloride ion.

A specific object of this invention is to provide ophthalmic solutions containing chlorhexidine gluconate which are unharmed by freezing and thawing.

Another specific object of this invention is to inhibit the formation of chlorhexidine hydrochloride in solutions containing both chlorhexidine gluconate and chloride ion.

DETAILED DESCRIPTION OF THE INVENTION

Figure 1:
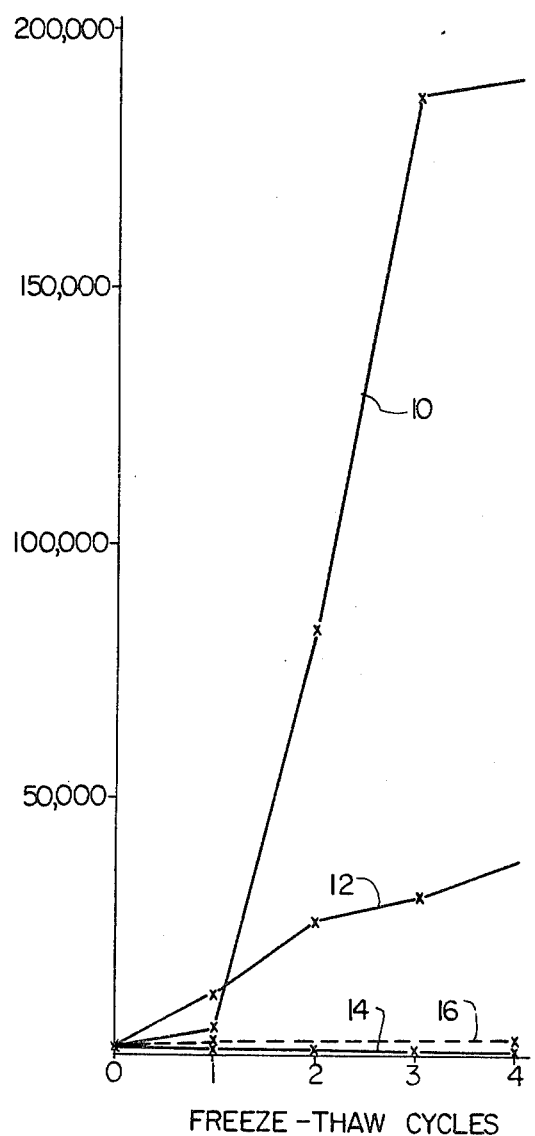
FIG. 1 is a graph of particle counts plotted against freeze-thaw cycles for solutions of chlorhexidine gluconate, chloride ion and varying amounts of a polyoxyethylene fatty acid ester.

Ophthalmic solutions containing chlorhexidine gluconate as a bactericide and chloride ion in the form of sodium chloride to provide isotonicity were found to become cloudy after undergoing one or more freeze-thaw cycles. That change in properties rendered the product unfit for sale or use.

An investigation into the cause of the cloudy appearance revealed that chlorhexidine gluconate precipitated out of solution as very finely divided particles of chlorhexidine hydrochloride upon freezing. These particles failed to redissolve upon thawing thus rendering the solution permanently cloudy in appearance. Thus, once chlorhexidine gluconate precipitates as the hydrochloride, the change is essentially irreversible.

It was found that addition of particular nonionic surfactants within certain ratios relative to the concentration of chlorhexidine gluconate prevented the precipitation of chlorhexidine gluconate as the hydrochloride upon exposure to long periods of freezing or to repeated freeze-thaw cycles. A sufficient amount of nonionic surfactant must be added to provide at least about 8, and preferably about 15, molecules of surfactant per molecule of chlorhexidine gluconate. Lesser amounts of surfactant not only fail to inhibit the precipitation of chlorhexidine hydrochloride but actually appear to promote the unwanted conversion. Amounts of surfactant greater than that required to prevent precipitation of chlorhexidine hydrochloride are generally undesirable as the properties of the ophthalmic solutions tend to be changed.

Surfactants useful in the practice of this invention comprise polyoxyethylene fatty acid esters having a hydrophile-lipophile balance (HLB) number greater than 11. Particularly preferred nonionic surfactants are the polyoxyethylene derivatives of long chain fatty acid partial esters of hexitol anhydride. These surfactants are commerically available from the Atlas Powder Company under the Tween trademark. However, the HLB number must be above 11. Thus, Tween 80 is an appropriate and preferred surfactant for use in this invention.

The exact mechanism by which precipitation of chlorhexidine gluconate as the hydrochloride is inhibited by the nonionic surfactant is not clearly understood. It is postulated however that an attraction between the oleate ester moity of the surfactant and the chlorhexidine molecule results in formation of a surfactant layer around each chlorhexidine molecule. This absorbed layer of surfactant molecules then stabilizes the chlorhexidine gluconate and prevents its precipitation as the hydrochloride.

The ophthalmic solutions to which this invention is particularly directed contain chlorhexidine gluconate at a concentration of about 0.005%. Surfactant concentrations on a weight or volume basis required to stabilize these solutions against changes upon freezing range from about 10 to 20 times the concentration of chlorhexidine gluconate, or about 0.05% to 0.1%. Surfactant concentrations less than about 0.05% are not effective to prevent formation of the hydrochloride while concentrations much greater than 0.1% tend to change the characteristics of the ophthalmic solutions.

The following examples will serve to illustrate specific embodiments of the invention.

EXAMPLE 1

An exemplary, commercially marketed, ophthalmic solution has the following composition:
Boric acid: 0.425%
Sodium borate: 0.054
Sodium chloride: 0.68
EDTA: 0.10
Thimerosal: 0.001
Chlorhexidine gluconate: 0.005
Water: balance This solution was subjected to freezing and was thereafter thawed. The solution prior to freezing was clear but had a distinctly cloudy appearance after the freeze-thaw cycle. The solution was then filtered and the precipitate was identified as chlorhexidine hydrochloride by infrared spectroscopy.

EXAMPLE 2

Four sample portions of the ophthalmic solution of Example 1 were prepared. A nonionic surfactnat comprising a polyoxyalkylene derivative of long chain fatty acid partial esters of hexitol anhydride (Tween 80) was added to the first sample portion in a concentration of 0.05% and to the second sample in a concentration of 0.1%. The last two sample portions were unaltered.

All four samples were analyzed for precipitated matter using a particle counter. Results were recorded as the total count of the particle population after 63.5 seconds of cumulative counting. In all cases, particle-free saline solution was used as a blank.

Thereafter, the first three samples were subjected to a series of freeze-thaw cycles. Samples were placed into and stored in a freezer at $-50°$ C., were removed from the freezer and thawed, and the thawed solutions were analyzed for precipitated matter using a particle counter as previously described. After analysis, the solutions were replaced in the freezer to begin the next freeze-thaw cycle.

Results of four of such freeze-thaw cycles are graphically presented in FIG. 1. Curve 10 represents the particle counts obtained by analysis of the ophthalmic solution without added surfactant. Curve 12 represents the analyses performed on the solution containing 0.05% surfactant and curve 14 represents the analyses performed on the solution containing 0.1% surfactant. For comparison purposes curve 16 represents analyses performed on the ophthalmic solution which neither has surfactant added nor was exposed to the freeze-thaw regimen.

As is clearly shown by the presented data, surfactant addition in the amount of 0.05%, or 10-fold the concentration of chlorhexidine gluconate, substantially decreased the amount of particulates formed during the freeze-thaw cycles. At a level of 0.1% surfactant addition, the particulate level was below that of unaltered ophthalmic solution stored at ambient conditions.

Figure 3:
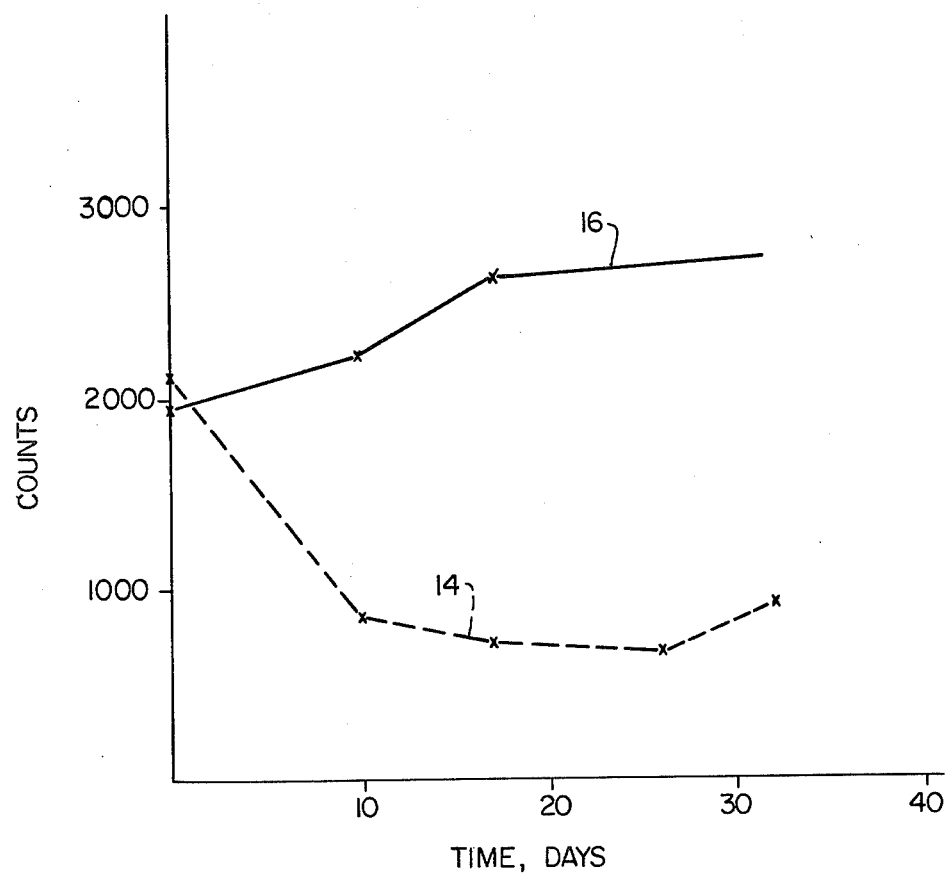
FIG. 3 is a graph illustrating the inhibition of chlorhexidine hydrochloride formation upon repeated freeze-thaw cycles.

FIG. 3 presents curves 14 and 16 of FIG. 1 on an expanded scale so as to illustrate the effect of surfactant addition in greater detail. As may be seen in this expanded view, the particulate count in the ophthalmic solution containing surfactant and subjected to multiple freeze-thaw cycles remained at a level some 40% of that displayed by the solution without added surfactant and not subjected to freezing and thawing.

EXAMPLE 3

Another group of four sample portions of the ophthalmic solution of Example 1 were prepared. A nonionic surfactant identical in composition to that used in Example 2 was added to the first sample portion in a concentration of 0.01%; to the second sample portion in a concentration of 0.05%; and to the third sample portion in a concentration of 0.1%. No surfactant addition was made to the fourth sample portion.

All four samples were analyzed for particulates as described in Example 2. All four samples were then subjected to a freeze-thaw regimen which differed from that of Example 2 in that the samples were allowed to remain frozen for a two-week period in the first freeze-thaw cycle.

Figure 2:
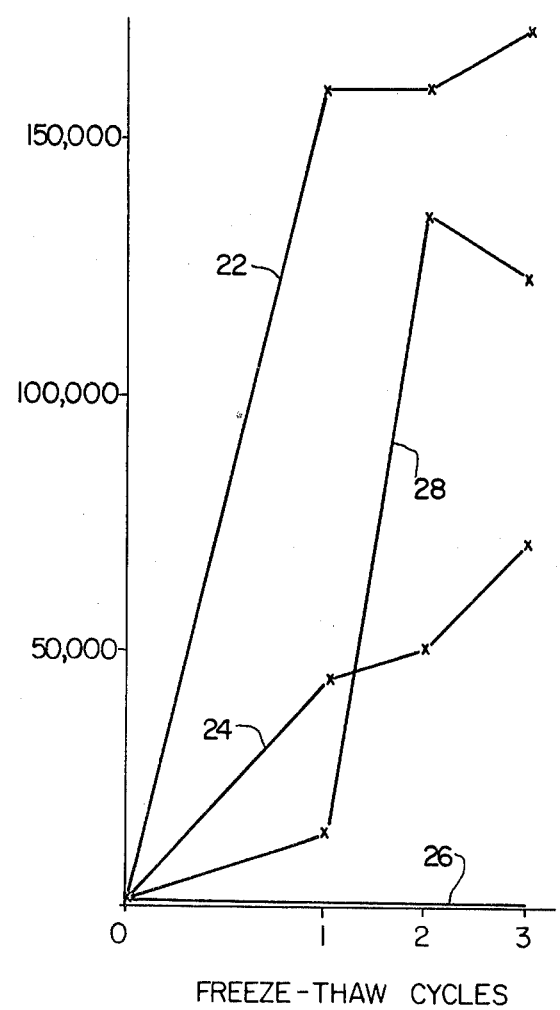
FIG. 2 depicts data similar to that of FIG. 1 further showing the effect of a lengthy freezing period.

The results obtained are presented in FIG. 2. In that Figure, curve 22 represents the ophthalmic solution with 0.01% added surfactant; curve 24 represents the ophthalmic solution with 0.05% added surfactant; curve 26 represents the ophthalmic solution with 0.1% added surfactant and curve 28 represents the ophthalmic solution alone without addition of surfactant. These data display the criticality of surfactant concentration; below about 0.05% or about 10 times the chlorhexidine gluconate concentration, the added surfactant not only fails to inhibit particulate formation but substantially increases it.

EXAMPLE 4

A study was conducted on albino rabbits to determine the toxicity and tolerance level of the surfactant used. To the ophthalmic solution of Example 1 was added the surfactant described in Example 2 in a concentration of 1.0%. Nine HEMA (hydroxyethyl methacrylate) contact lenses (43% water) were soaked in the solution with stirring for 18 hours or more each day for 5 days. Three lenses were alternately inserted into one eye of each of 3 rabbits for two to three hours per day. The rabbits showed no significant eye irritation during this study.

What is claimed is:

1. A method for preventing the precipitation of chlorhexidine gluconate from a chloride ion-containing aqueous solution thereof upon exposure to freezing which comprises adding to the solution a polyoxyethylene fatty acid ester having an HLB number greater than 11 in a concentration greater than about 0.05% and less than about 0.1% but at least 10 times that of the chlorhexidine gluconate.

2. The method of claim 1 wherein said solution comprises an ophthalmic solution containing chlorhexidine gluconate in a concentration of about 0.005%.

3. The method of claim 2 wherein said fatty acid ester is a partial ester of hexitol anhydride.

4. The method of claim 2 wherein said ophthalmic solution contains sodium chloride in an amount sufficient to provide isotonicity.

* * * * *